United States Patent
van Amerongen et al.

(10) Patent No.: US 6,492,538 B1
(45) Date of Patent: Dec. 10, 2002

(54) METHOD OF MANUFACTURING A STEROL ESTER MIXTURE

(75) Inventors: Marnix P van Amerongen; Lourus Cornelis Lievense; Cornelis Willem Van Oosten, all of Vlaardingen (NL)

(73) Assignee: Lipton, division of Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 09/202,899

(22) PCT Filed: Jun. 27, 1997

(86) PCT No.: PCT/EP97/03494

§ 371 (c)(1),
(2), (4) Date: Jan. 18, 2000

(87) PCT Pub. No.: WO98/01126

PCT Pub. Date: Jan. 15, 1998

(30) Foreign Application Priority Data

Jul. 5, 1996 (EP) .............................. 96201871
Dec. 19, 1996 (EP) ............................. 96203643

(51) Int. Cl.[7] .............................................. C07C 53/00
(52) U.S. Cl. ........................ 554/229; 554/156; 554/195; 426/478; 426/489
(58) Field of Search ................................ 554/156, 229, 554/195; 426/478, 489

(56) References Cited

U.S. PATENT DOCUMENTS 4,748,161 A * 5/1988 Kimura et al. .............. 514/182
5,290,579 A * 3/1994 Hitotsumatsu et al. ...... 426/489

* cited by examiner

Primary Examiner—Deborah D. Carr
(74) Attorney, Agent, or Firm—Gerard J. McGowan, Jr.

(57) ABSTRACT

Process for the manufacture of a mixture of fatty acid esters comprising the steps of:
  (a) hydrolysing a sterol ester or a mixture of sterol esters such that a mixture is obtained comprising phenolic acids and/or fatty acids, and free sterols; and
  (b) optionally, separating the phenolic acids and/or fatty from the reaction mixture; and
  (c) esterifying the so obtained free sterols with particular fatty acids.

18 Claims, No Drawings

METHOD OF MANUFACTURING A STEROL ESTER MIXTURE

The present invention relates to a method for the manufacture of an ester mixture, in particular an ester mixture of phytosterols and phytostanols (4-desmethylsterols, 4-monomethylsterols and 4,4'-dimethylsterols and their stanol equivalents) (hereinafter called sterols) and fatty acids.

High cholesterol levels in blood serum can cause an increased risk of coronary heart diseases. Several methods have been proposed for reducing cholesterol levels.

A well-known method relates to a careful selection of fatty acids in the diet, in particular a diet rich in unsaturated fatty acids can help to reduce cholesterol levels.

Another method relates to the addition of specific substances to the diet to lower the cholesterol level. For example WO 92/19640 disloses the use of β-sitostanol ester for lowering cholesterol levels in serum.

It was found that particular sterol derivatives have better cholesterol lowering properties than others. A number of sterols occur in nature which are esterified. For example, the majority of sterols, i.e. 25–80%, found in sources like corn, wheat, oat, rice bran and sheanut are esterified with phenolic acids such as ferulic acid, coumaric acid, caffeic acid, and cinnamic acid. However, it has been found that these esterified sterols are less suitable for lowering cholesterol-levels in serum.

This means that for the majority of sterol derivatives occurring in sources like corn, wheat, oat, rice bran and sheanut, there is a desire for improvement for their blood cholesterol lowering effects.

Further, it has been found that a significant part of sterols is not esterified at all. This type of sterols is not easily soluble in oils, and so not very suitable as a good source for applications in fat based food products.

U.S. Pat. No. 3,751,569 suggests the use of esters of monocarboxylic acid and plant sterols in dietary oils for reducing the cholesterol level.

A disadvantage of the methods of WO 92/19640 and U.S. Pat. No. 3,751,569 is the high costs of the ester materials. These high costs are due to the high isolation and preparation costs for the materials.

All methods known to day for making ester materials use free sterols as occurring in nature as the starting material for obtaining ester mixtures. Also, in nature, a number of sterol esters exists that were found that are not as effective in blood cholesterol lowering as the fatty acid esters of phytosterols and phytostanols.

Where in this application sterols are mentioned, phytosterols, phytostanols or mixtures thereof are meant. Hence, the term sterols in this application refers to 4-desmethylsterols, 4-monomethylsterols and 4,4'-dimethylsterols, their stanol equivalents, and mixtures thereof in any of combination possible.

The present invention aims at providing a cheap process for the preparation of an ester mixture, said ester mixture having a cholesterol lowering effect on foods. By the presently found method, it is now possible to have all sterols and sterol derivatives present in fat rich sources, but which up till now were not suitable for obtaining sterol derivatives that have a significant blood cholesterol lowering effect. Moreover, the blood cholesterol lowering effect obtainable by the use of the total amount of sterols and sterol derivatives present in these sources was found to be increased. Thus, the amount of effective cholelesterol lowering sterol derivatives obtainable from sources used in the past is increased, and many more sources applicable for obtaining such effective sterol derivatives have become available.

It has been found that the costs for producing the ester mixture can significantly be reduced if materials other than free phytosterols (U.S. Pat. No. 3,751,569) or their derivatives (WO 92/19640) are used as the starting material and the process involves a specific hydrolysation step.

Further advantages of the process of the invention are that the process can be carried out without the need for high investments, the process can easily be carried out at a high yield and the level of wastage is low, because the by-products can be used for other purposes.

Further advantages are that the specific ester mixture obtained by the process of the invention can very conveniently be incorporated in food products at relatively high levels. They also show excellent abilities to reduce serum cholesterol levels.

Accordingly in a first aspect the present invention relates to a process for the manufacture of an ester mixture comprising the steps of:

(a) hydrolysing a sterol ester or a mixture of sterol esters such that a mixture is obtained comprising phenolic and/or fatty acids, and free sterols; and (b) esterifying the so obtained free sterols with particular fatty acids.

In another aspect, the invention relates to a process for the manufacture of an ester mixture comprising the steps of:

(a) hydrolysing a sterol ester or a mixture of sterol esters such that a mixture is obtained comprising phenolic acids and/or fatty acids, and free sterols; and (b) separating the phenolic acids and/or fatty from the reaction mixture; and (c) esterifying the so obtained free sterols with particular fatty acids.

The method is very beneficial if the sterol esters are esters of sterols and acids other than fatty acids. In this embodiment, the sterol ester or mixture of sterol esters is a mixture comprising phenolic acid sterol esters. In a further preferred embodiment, the process is a process wherein the sterol ester or mixture of sterol esters consist of a phenolic acid sterol ester or a phenolic acid sterol ester mixture.

In a particular embodiment the invention concerns a process for the manufacture of an ester mixture comprising the steps of:

(a) hydrolysing γ-oryzanol such that a mixture is obtained comprising ferulic acid and sterols; and (b) separating the ferulic acid from the reaction mixture; and (c) esterifying the so obtained sterols with particular fatty acids.

In particular, the present invention encompasses sterol fatty acid ester mixtures obtainable by the method of the present invention. If in the process of the invention, sterols of one particular source are used without modification, the nature and tatio of the sterols found in the product resulting from the process of the present invention will be indicative of the source used. In one embodiment of the present invention, the sterol fatty acid ester mixtures is characterised by the nature of the type of sterols found in the sterol esters and the ratio of the different sterol, the nature and ratio being similar to those found in the sterol derivatives present in rice bran.

In yet another embodiment, nature and ratio of the alcohol part found in the sterol fatty acid ester mixture of the invention are similar to those found in the sterol derivatives present in shea.

In the case there is a desire to prepare fatty acid sterol esters of a further definked fatty acid type, the process indicated above can also be applied for re-esterifying fatty acid sterol esters with a further defined group of fatty acids. With particular fatty acids is meant in this application a group of fatty acids chosed as desired.

In a most preferred embodiment of this invention, sterol esters are used that are esterified with any phenolic acid. In nature, most phenolic acid sterol esters are esters of sterols and phenolic acids from the group of ferulic, coumaric, caffeic, and cinnamic acid.

Sterol esters that are in particular suitable for the method of the present invention are the sterol esters from rice bran and from sheanut.

The sterol esters and stanol esters can be isolated from natural sources by known techniques. If so desirable, the sterol esters can be hardened to stanol esters, before or after the process of re-esterification.

A particular suitable sterol esters group to be re-esterified is oryzanol. Oryzanol or γ-oryzanol is a mixture of ferulic acid esters of mainly the phytosterols campesterol, β-sitosterol, 24-methyl-cycloartenol and cycloartenol. γ-oryzanol is present as a minor component at relatively high levels in rice-bran oil.

A very suitable method method of obtaining oryzanol is described in our co-pending European Patent Application No. 96201871.9. Preferably the starting material is the by-product of the alkali refining process of rice bran oil, the so called soap stock.

Another particular suitable sterol ester, group to be re-esterified is the group of sterol esters found in sheanut, a mixture of mainly cinnamic acid esters of mainly the phytosterols alpha-amyrin, beta-amyrin, lupeol, butyrospermol and germanicol.

A very suitable method method of obtaining sheanut sterols is described in our co-pending European Patent Application 96304994.5.

The process now found has the further advantage that it can be applied to a mixture of sterols and sterol derivatives from a particular source or a mixture of different sources. For example, a mixture can be applied as occurring in a natural source, e.g. a sterol concentrate obtained by concentrating the sterol rich part of an oil, without the need for isolation of one or more specific sterols prior to subjecting it to the process of the present invention. In this embodiment, fatty acid sterol esters and phenolic acid sterol esters are re-esterified with fatty acids, and any free sterol esters present in such a composition will be esterified to fatty acid sterol esters. Accordingly, a large amount or even all of the sterols present in such a natural source are processed in such a manner that they become available as effectively cholesterol lowering sterol derivatives.

It is preferred that the sterol ester or sterol ester mixture used in the process of the invention is of food-grade quality i.e. it is in pure form or in the form of a food-grade concentrate, for example a concentrated solution of sterol esters or of sterols comprising sterol esters in a solvent e.g. a natural oil. Especially preferably the level of sterol esters in the starting mixture is from 5 to 90%, and preferably from 40–90%.

The first step of the process of the invention relates to the hydrolysation of the sterol esters. This hydrolysation is aimed at the separation of the acid group from the methylsterol group. This hydrolysation can be carried out by any suitable method for hydrolysing. Suitable conditions for the hydrolysation reaction are for example described in EP 503 650. Other conditions are illustrated in the example. It is believed to be well within the ability of the skilled person to find possible variation in processing conditions to carry out the hydrolysation reaction.

Preferably the hydrolysation reaction is carried out until at least 50 wt % of the sterol esters are split in the corresponding free acid and free sterols, more preferred at least 80 wt %, most preferred 90 to 100 wt %. For example, in case γ-oryzanol is used, the hydrolysation reaction is carried out until at least 50 wt % of the γ-oryzanol is split in the corresponding ferulic acid and sterols, more preferred at least 80 wt %, most preferred 90 to 100 wt %.

Suitable esters are sterol esters as found in natural sources such as wheat, corn, rice bran, oat, and sheanut. These sterol esters can be esters of phenolic acids such as ferulic, coumaric, caffeic, and cinnamic acid. The sterols can be phytosterols and phytostanols (4-desmethylsterols, 4-monomethylsterols and 4,4'-dimethylsterols and their stanol equivalents), hereinafter referred to as sterols.

After hydrolysation a mixture is obtained containing one or more phenolic acids and or one or more fatty acids and one or more sterols. In its preferred embodiment, the phenolic acids obtained are a by-product and not needed for further processing they could be conveniently removed from the reaction mixture. In the embodiment that fatty acid sterol esters are hydrolysed, it may also be desired to remove the fatty acids obtained after hydrolysation to allow specific fatty acid sterol esters to be obtained by esterification of the sterols with these particular fatty acids.

In case a mixture of phenolic acid sterol esters and fatty acid sterol esters (and optionally, free sterols being present) are hydrolysed, a further embodiment would also comprise the removal of any of the phenolic and fatty acids obtained by the hydrolysation process. Any of these removal steps is preferably carried out prior to esterification of the free sterols obtained with the desired particular fatty acids.

The removal can take place in any stage of the process, however for avoiding possibly occurring backward reactions with the sterols it is preferred that the phenolic acid(s) is removed from the reaction mixture before further reacting by esterification. Removal of the phenolic acid and/or fatty acid can be done by any sautable technique e.g. filtering or precipitation. EP 503 650 describes suitable methods for the removal of ferulic acid which can also be applied to other phenolic acids. Other methods are illustrated in the examples.

If the estrification is carried out under such conditions that the fatty acids are, compared to the phenolic acids, (largely) selectively estrified to the sterols, separation of the phenolic acids is not required. In this particular embodiment it may be desired to use an enzymatic (selective) esterification process.

The process of the invention also involves the esterification of the methylsterol mixture obtained in the hydrolysis reaction. Preferably the sterols are esterified with one or more $C_{2-22}$ fatty acids. Such fatty acid groups will form an ester bond at the former attachment point of the phenolic acid. For the purpose of the invention the term $C_{2-22}$ fatty acid refers to any molecule comprising a $C_{2-22}$ main chain and at least one acid group. Although not preferred within the present context the $C_{2-22}$ main chain may be partially substituted or side chains may be present. Preferably, however the $C_{2-22}$ fatty acids are linear molecules comprising one or two acid group(s) as endgroup(s). Most preferred are linear $C_{8-22}$ fatty acids as occur in natural oils.

Suitable examples of any such fatty acids are acetic acid, propionic acid, butyric acid, caproic acid, caprylic acid, capric acid. Other suitable acids are for example citric acid, lactic acid, oxalic acid and maleic acid. Most preferred are lauric acid, palmitic acid, stearic acid, arachidic acid, behenic acid, oleic acid, cetoleic acid, erucic acid, elaidic acid, linoleic acid and linolenic acid.

When desired a mixture of fatty acids may be used. For example it is possible to use a natural occurring fat or oil as a source of the fatty acid and to carry out the esterification via an interesterification reaction.

In a particular emobodiment, the fatty acid mixture contains a high amount (>35%, preferably >45%, further preferred >70%) of polyunsaturated fatty acids (PUFA). This does not only provide the advantage of PUFA itself having good blood cholesterol lowering capacity, but also of the sterols esters prepared with such fatty acids being considered as having a higher solvability and blood cholesterol lowering efficacy in the body.

Preferably fatty acid mixtures of rice bran oil, sunflower, safflower, rapeseed, linseed, linola and/or soybean are used. These are typical sources of high PUFA and/or low SAFA.

Suitable eaterification conditions are for example described in WO 92/19640. Further suitable conditions are given in the examples below.

Preferably the conditions of the esterification reaction are chosen such that at least 50 wt %, preferably at least 75 wt % most preferred from 90–100 wt % of the sterols are esterified.

In the particular embodiment where γ-oryzanol is used, the reaction will result in a mixture containing esters of sterols, said sterols comprising at least two sterols selected from the group of campesterol, β-sitosterol, 24-methylene cyclo-artenol and cyclo-artenol.

Preferably at least 50%, more preferred more than 80 wt %, most preferred from 90 to 100% of the sterols is selected from the group of campesterol, β-sitosterol, 24-methylene cyclo-artenol and cyclo-artenol.

Especially preferably the mixture of fatty acid esters of sterols is obtained by subjecting a mixture of (a) 5–40 wt % campesterol
(b) 2–25 wt % β-sitosterol
(c) 20–60 wt % 24-methylene cyclo-artenol; and
(d) 10–50 wt % cyclo-artenol to the process of the present invention.

In another especially preferred embodiment, the mixture of esters of sterols comprises at least 50% of the sterols selected from the group of alpha-amyrin, beta-amyrin, lupeol, butyrospermol and germanicol.

In this embodiment a further preference exists for the mixture of fatty acid esters of sterols being obtained by subjecting a mixture of (a) 2–45 wt % alpha-amyrin
(b) 0.2–25 wt % beta-amyrin
(c) 0.2–35 wt % lupeol
(d) 2–45 wt % butyrospermol and
(e) 0.1–15 wt % germanicol to the process of the present invention.

Preferably the mixture obtained by esterification is added to food products in an amount of 0.5 to 40 wt, more preferred 2 to 30 wt %, most preferred 3 to 20 wt %, with a particular preference for 4–20 wt %. Surprisingly the use of these relatively high levels of the fatty acid sterol esters does generally not lead to sandiness of the product. Although applicants do not wish to be bound by any theory it is believed that this reduction of sandiness may be caused by a decrease of amount and/or rate of crystallisation of the ester components compared to free sterols.

Especially preferably the ester mixtures of the invention are added to fat based food products. Fat based food products are food products (partially) based on fat and regarded by the user, in particular the consumer, as 'fatty type of products'. Examples are margarines, butter, yellow fat spreads (containing vegetable fat and/or animal fat such as butterfat), dressings, mayonnaise, cheese, shortenings, cooking and frying oils and the like. These products in most cases comprise a particular amount of fat. In some cases, however, products are still regarded as 'fatty type of products', despite a replacement of part or even all the fat by fat replacers. Fat based food products in which the fat is partially or completely replaced by fat replacers are also covered by the term fat based food products of this invention.

Fat products consisting of fat only are also considered as fat based food products in this specification. These are not only used as cooking and frying oils, but also sometimes in the industry in the preparation of food products, e.g. in baking.

The food products as such are common products in the western world, and are used by consumers on a daily basis in amounts different for each individual.

The invention is in particular very suitable for yellow fat spreads, dressings, cheese, shortenings and cooking and frying oils, and more in particular for yellow fat spreads which can comprise 0 (zero) to 90 wt % fat (usually 5–80 wt %). Dressings can comprise 0 to 85 wt % fatty (usually 5–80 wt %), shortenings, cooking and frying oil more than 95 wt % fat. In a particular embodiment of this invention, the fat based food product is selected from the group of margarines, butter and spreads.

Yellow fat spreads comprising less than 80 wt % fat and at least 2.0 wt % of the ester mixture can be regarded as very beneficial in that these not only have a very low fat content, but also show a significant lowering of the blood cholesterol working if applied similar to a common butterlike spread on a regular, daily basis. This applies even more for products with less than 60 wt % fat. In another embodiment, the spread comprises at least 3 wt % of the ester mixture. In a particular embodiment thereof, the spread comprises at least 5 wt % of the ester mixture, the ester mixture preferably being obtained by a process in which the sterol ester (mixture) to be hydrolyzed comprises oryzanol.

Another advantage of the present invention is that by addition of the mixture obtained by esterification the amount of hardstock required to make a spreadable product out of above mentioned liquid oils can be reduced, thereby optimizing the amount of PUFA rich glycerides in the product.

The use of the ester mixture in cheese shows an additional beneficial effect, which is that the cholesterol in cheese is adsorbed by the body in a far lesser amount if the ester mixture is present in the cheese than without. Hence, whereas cheese consumption usually adds cholesterol to the body, with the use of the ester mixture a strongly reduced absorbtion and a blood cholesterol lowering effect will be found. This effect can also be found for food products other than cheese comprising cholesterol or consumption of cholesterol containing food products in combination with the products as described in the invention. The amount of ester mixture to be added on the preparation of the cheese is preferably higher than the amount of cholesterol on a molar weight basis, so that the cheese product obtained still contains the ester mixture in a free and active form.

The fat that is applied in these fat based food products can be any fat, such as dairy fat and/or vegetable fat. However, if fat is present, for health reasons the use of one or more vegetable fat sources is preferred. In particular, the use of liquid fats is preferred. These can be hydrogenated, interesterified, and the like. The fat can be one single fat or a blend.

The use of fat compositions comprising a considerable amount of pufa rich triglycerides in addition to the use of the ester mixture is in particular considered highly beneficial. For example, oils of sunflower, safflower, rapeseed, linseed, linola and/or soybean can be used in a preferred embodiment.

If a fat blend is used, it is preferred that it comprises at least 30%, and more preferred at least 45% of polyunsaturated fatty acids, based on the total weight amount of the fat in the fat based food product. So, a strong effect on the cholesterol lowering effect is obtained if use is made of a mixture of the ester materials of the invention or these components in combination with the antioxidants like polyphenols and tocopherols, or extracts comprising all of these these components in a food product in which a fat blend comprising at least 30 wt. % of pufa rich triglycerides is used.

The invention further envisages the use of an oil concentrate comprising more than 4 wt % of the ester mixture for the preparation of a fat based food product as described above. In another preferred embodiment, the invention concerns the use of an oil concentrate comprising more than 4 wt % of the ester mixture for the preparation of a yellow fat spread as described above.

Particular advantages are found when a fat based food product is prepared using 0.5–40 wt %t of an ester mixture which is obtained by subjecting a mixture of (a) 5–40 wt % campesterol (b) 2–25 wt % β-sitosterol (c) 20–60 wt % 24-methylene cyclo-artenol; and (d) 10–50 wt % cyclo-artenol to the process of the present invention, or, alternatively, by using 0.5–40 wt % of an ester mixture which is obtained by subjecting a mixture of (a) 2–45 wt % alpha-amyrin (b) 0.2–25 wt % beta-amyrin (c) 0.2–35 wt % lupeol (d) 2–45 wt % butyrospermol and (e) 0.1–15 wt % germanicol to the process of the present invention.

In addition to the ester mixture as described above, food products of the invention may comprise further ingredients which can have positive effects on the health. Examples of these are for example anti-oxidants e.g. polyphenols or tocopherols and tocotrienols.

The invention will now be further illustrated by means of the following examples:

EXAMPLE I

Preparation of the Ester Mixture

A crude soapstock is prepared by chemically refining rice bran oil by addition of sodium lye (4M) followed by isolating the aqueous bottom layer. The oil layer is washed twice with water and the washing are combined with the first washing.

The resulting crude soapstock contains per 500 ml:

12.5 g γ-oryzanol 5.5 g alkali salts of free fatty acids 32 g tri-acyl glycerols surplus sodium lye balance water The γ-Oryzanol contained 4 esters of ferulic acid and the following sterols:

24.6 wt % campesterol 15.5 wt % β-Sitosterol 31.2 wt % 24-methyl cycloartenol 28.7 wt % cycloartenol The ester mixture can be obtained from the crude soapstock as follows:

500 ml of crude soap stock can be concentrated to 100 ml by evaporation, followed by the addition of 0.15 mol sodium hydroxide dissolved in a small amount of water and 200 ml ethanol. Upon boiling this mixture for about 2 hours, a nearly complete saponification (over 90%) of the γ-Oryzanol and the tri-acylglycerols will take place. After the reaction is completed most of the ethanol can be removed by evaporation.

The mixture is acidified by addition of 400 ml distilled water containing approx. 0.3 mol hydrocloric acid. After separation of the layers, the ferulic acid as well as the glycerol are collected in the aaqueous bottom layer. The top layer containing the fatty acids and the sterols, can then be washed with water until neutral. The toplayer is then dried by evaporating the water under vacuum (95° C. at 5 mm for about 1 h).

The resulting mixture of sterols and fatty acids can then be esterified by addition of methanol (4 times volume of other methylsterol fraction) and 0.2% of 96% sulfuric acid. The mixture is boiled for 2 hours, this results in the formation of methylesters of the fatty acids, while the sterols do not react. The lipid fraction of the mix is isolated and dried and contains the sterols and the methylesters of fatty acids.

The esterification step of the sterols then takes place by adding 0.05 wt % of sodium methoxide and heating gradually to 130° C. under vacuum (approx. 5 mm Hg) and constant stirring, for about 2 h, which results in interesterification of the methylesters with the sterols. The catalyst is destroyed by addition of some water. After fiphase separation the resulting esters of sterols and fatty acids can be isolated and subjected to molecular distilliation to remove the surplus of fatty acid methylesters.

The resulting ester mixture has the same ratio of components as indicated above.

EXAMPLE II

Example I can be repeated whereby the hydrolisation of the crude soap stock takes place in an autoclave at 180° C. at 8–10 bar, and in the presence of a suitable catalyst.

EXAMPLE III

The ester mixture obtained in example I can be incorporated in a 70% fat spread as follows:

44 parts refined sunflower oil (65% PUFA as linoleic acid) was enriched with the ester mixture of example 1 and mixed with 20 parts of normal refined sunflower oil and 6 parts of a refined interesterified mixture of 50 parts fully hardened palm oil and 50 parts fully hardened palm kernel oil. To 70 parts of this fatblend, 0.1 part soybean lecithin, 0.1 part monoglyceride and 0.1 part of β-carotene solution are added.

To 29 parts water, 0.3 part whey protein powder, a small amount of flavour, and citric acid to obtain a pH of 4.8 are added.

70 parts of the fat phase composition and 30 parts of the aqueous phase composition were mixed and kept at 60° C. The mixture was then passed through a Votator line with 2 scraped surface heat exchangers (A-units) and 1 stirred crystallizer (C-unit) in AAC-sequence operating at 800, 800 and 100 rpm respectively. The product leaving the C-unit had a temperature of 11° C. It was filled into tubs and stored at 5° C. A good and stable, high PUFA, high fat-continuous spread enriched with 12% of the ester-mixture was obtained.

EXAMPLE IV

Preparation of a Spread 40%

35 parts refined sunflower oil (65% PUFA as linoleic acid) can be enriched with the ester mixture of example II and mixed with 5 parts of a refined interesterified mixture of 50 parts fully hardened palm oil and 50 parts fully hardened palm kernel oil. To 39 parts of this fatblend, 0.1 part soybean lecithin, 0.1 part monoglyceride and a small amount of β-carotene solution are added.

To 57 parts water, 2 parts gelatine, 0.3 part whey protein powder, a small amount of flavour, preservative and citric acid to obtain a pH of 4.7 are added.

40 parts of the fat phase composition and 60 parts of the aqueous phase composition are mixed and kept at 60° C. The mixture can then be passed through a Votator line with 2 scraped surface heat exchangers (A-units) and 2 stirred crystallizers (C-unit), in ACAC-sequence operating at 500, 1000, 600 and 100 rpm respectively. The product leaving the last C-unit has a temperature of 10° C. It is filled into tubs and stored at 5° C. A good and stable, high PUFA, low fat-continuous spread enriched with 7% of the ester mixture is obtained.

EXAMPLE V

Preparation of a Dressing 33% Fat 55 parts of water is mixed with 11 parts of various flavour components, preservatives, thickeners and emulsifiers. The amixture is thouroughly mixed in a stainless steel stirred vessel. To this aquous mixture 33 parts of sunflower oil (65% PUFA as linoleic acid) enriched with the ester mixture as described in Example 1 and a 2% free phytosterol mixture is added, thoroughly mixed for an additional 15 min, to obtain a pre-emulsion. The pre-emulsion is brought into a colloid mill (Prestomill PM30) and processed at a split-size between level 15 and 20 and a throughput between level 4 and 6. A good and stable water continuous dressing enriched with 10% of the ester mixture and 2% free phytosterol mixure is obtained.

What is claimed is:

1. Process for the manufacture of a mixture of and ester mixture comprising the steps of:
   (a) hydrolysing a sterol ester or a mixture of sterol esters such that a mixture is obtained comprising phenolic and/or fatty acids, and free sterols; and
   (b) esterifying the so obtained free sterols with particular fatty acids.

2. Process according to claim 1, comprising the steps of
   (a) hydrolysing a sterol ester or a mixture of sterol esters such that a mixture is obtained comprising phenolic acids and/or fatty acids, and free sterols; and
   (b) separating the phenolic acids and/or fatty from the reaction mixture; and
   (c) esterifying the so obtained free sterols with particular fatty acids.

3. Process according to claim 1, wherein the sterol ester or mixture of sterol esters is a mixture comprising phenolic acid sterol esters.

4. Process according to claim 1, wherein the sterol ester or mixture of sterol esters consist of a phenolic acid sterol ester or a phenolic acid sterol ester mixture.

5. Process according to claim 1, wherein the sterol ester or sterol ester mixture is present in the reaction mixture at a concentration of 5 to 90 wt %.

6. Process according to claim 1 wherein the phenolic acid and or fatty acid originating from the sterol ester starting material is separated from the reaction mixture prior to esterification.

7. Process according to claim 1 wherein the sterols are esterified to $C_{2-22}$ fatty acids sterol esters.

8. Process according to claim 1 wherein the sterols are esterified to $C_{8-22}$ fatty acids sterol esters.

9. Process according to claim 1 wherein the sterols are esterified to fatty acid sterol esters of rice bran oil, sunflower, safflower, rapeseed, linseed, linola and/or soybean.

10. Process according to claim 1 in which the starting material is obtained from rice bran.

11. Process according to claim 1 wherein the starting material is obtained from sheanut.

12. Mixture of fatty acid esters of sterols obtainable by the process of claim 1.

13. Mixture of fatty acid esters of sterols, characterized in that the mixture is obtained by subjecting a mixture of
   (a) 5–40 wt % campesterol
   (b) 2–25 wt % β-sitosterol
   (c) 20–60 wt % 24-methylene cyclo-artenol; and
   (d) 10–50 wt % cyclo-artenol
to the process of claim 1.

14. Mixture of fatty acid esters of sterols, characterized in that the mixture is obtained by subjecting a mixture of
   (a) 2–45 wt% alpha-amyrin
   (b) 0.2–25 wt % beta-amyrin
   (c) 0.2–35 wt % lupeol
   (d) 2–45 wt % butyrospermol and
   (e) 0.1–15 wt % germanicol
to the process of claim 1.

15. Fat based food product comprising 0.5 to 40 wt % of an ester mixture obtainable by the process of claim 1.

16. Fat based food product according to claim 15 selected from the group-of margarines, butter, spreads, mayonnaise, dressings, shortenings, cooking and frying oils.

17. Fat based food product according to claim 16, the product being selected from the group of margarines, butter and spreads.

18. Fat based food product according to any on of claims 15–17, characterized in that the product comprises 0.5–40 wt % of an ester mixture of claim 13.

* * * * *